(12) United States Patent
Soper et al.

(10) Patent No.: US 9,272,977 B2
(45) Date of Patent: Mar. 1, 2016

(54) PURIFICATION OF SUCCINIC ACID FROM FERMENTATION BROTH ON NON-FUNCTIONALIZED CHROMATOGRAPHIC RESIN

(71) Applicant: ARCHER DANIELS MIDLAND COMPANY, Decatur, IL (US)

(72) Inventors: John G. Soper, Mt. Zion, IL (US); Mitchell Schultz, Decatur, IL (US); Thomas P. Binder, Decatur, IL (US)

(73) Assignee: Archer Daniels Midland Company, Decatur, IL (US)

(*) Notice: Subject to any disclaimer, the term of this patent is extended or adjusted under 35 U.S.C. 154(b) by 0 days.

(21) Appl. No.: 14/399,028

(22) PCT Filed: Apr. 17, 2013

(86) PCT No.: PCT/US2013/036858
§ 371 (c)(1),
(2) Date: Nov. 5, 2014

(87) PCT Pub. No.: WO2013/169447
PCT Pub. Date: Nov. 14, 2013

(65) Prior Publication Data
US 2015/0158803 A1  Jun. 11, 2015

Related U.S. Application Data

(60) Provisional application No. 61/643,405, filed on May 7, 2012.

(51) Int. Cl.
C07C 51/47 (2006.01)
C07C 51/42 (2006.01)
B01D 15/32 (2006.01)
B01D 15/42 (2006.01)
C12P 7/46 (2006.01)

(52) U.S. Cl.
CPC .............. C07C 51/47 (2013.01); B01D 15/327 (2013.01); B01D 15/426 (2013.01); C07C 51/42 (2013.01); C12P 7/46 (2013.01)

(58) Field of Classification Search
CPC .... C07C 51/47; B01D 15/327; B01D 15/426; C12P 7/46
See application file for complete search history.

(56) References Cited

U.S. PATENT DOCUMENTS

| 5,407,580 A | * | 4/1995 | Hester et al. ................... 210/635 |
| 5,786,185 A | * | 7/1998 | Tsao et al. ..................... 435/139 |
| 6,391,204 B1 | * | 5/2002 | Russo, Jr. ....................... 210/635 |

FOREIGN PATENT DOCUMENTS

WO  WO2011/082378  *  7/2011

OTHER PUBLICATIONS

Efe et al, Chemical Engineering and Processing, 50(2011), 1143-1151.*

* cited by examiner

*Primary Examiner* — Shailendra Kumar
(74) *Attorney, Agent, or Firm* — Vincent T. Kung (57) ABSTRACT

A process for purifying a filtered fermentation broth of succinic acid is described. The process involves separating succinic acid from the other organic acids and salts in a raw filtered broth using a non-functionalized chromatographic resin. The operation can be run either as an isocratic elution to yield free succinic acid, or as a gradient or binary elution to produce succinate salt.

20 Claims, 8 Drawing Sheets

PURIFICATION OF SUCCINIC ACID FROM FERMENTATION BROTH ON NON-FUNCTIONALIZED CHROMATOGRAPHIC RESIN

BENEFIT OF PRIORITY

The present application claims benefit of priority of International Application No. PCT/US13/36858, filed Apr. 17, 2013, which claims priority to U.S. Provisional Patent Application No. 61/643,405, filed May 7, 2012, of which the entire contents of each are incorporated herein by this reference.

FIELD OF THE INVENTION

The present invention relates to a process for the separation of succinic acid and/or dibasic succinate from a fermentation broth. In particular, the invention pertains to a method of purifying succinic acid and/or its salt that involves using chromatography on non-functionalized resins.

BACKGROUND

Succinic acid and its derivatives are useful platform chemicals that are widely used in the manufacturing of polymers, fuel additives, inks, cosmetics, and as additives in foods and pharmaceuticals. For example, succinic acid can be used as an input In the production of pigments, solvents, detergents, metal plating and polybutylene succinate polymers, which can be used to replace conventional plastics in applications such as flexible packaging, agricultural films and compostable bags.

Succinic acid has been traditionally produced from petrochemicals which are limited, costly and cause pollution problems. One to the variety of* applications, alternative methods of producing bio-succinic acid have received attention in the past few years. A more environmentally friendly approach that has gained much interest is the fermentative production of succinic acid from glucose by anaerobic bacteria. The fermentative production of succinic acid can be regarded as a green technology not only because renewable substrates are used for its production, but also $CO_2$ is incorporated into succinic acid during fermentation. Thus, fermentative succinic acid contributes a green, bio-derived feedstock for the manufacture of synthetic resins, biodegradable polymers, and chemical intermediates.

Although the fermentative production of succinic acid has several advantages over petrochemical-based processes, for the biotechnological process to be competitive with petrochemical production one desires to minimize the production costs. (See e.g., James McKinlay et al., "Prospects for a Bio-based Succinate Industry," APPL. MICROBIOL. BIOTECHNOL, (2007) 76:727-740; incorporated herein by reference). About 60% of the total production costs are generated by downstream processing, e.g., the isolation and purification of the product in the fermentation broth. The purification of succinic acid from fermentation broths is a critical step in the development of a successful, cost effective process to recover the acid.

Over the years, various approaches have been developed to isolate succinic acid. These techniques have involved using ultra-filtration, precipitation with calcium hydroxide or ammonia, crystallization, electrodialysis, liquid-liquid extraction, sorption and ion exchange chromatography. (See, Tanja Kurzrock et al., "Recover of Succinic Acid from Fermentation Broth," Review, BIOTECHNOLOGY LETTER, (2010) 32:331-339; incorporated herein by reference.) A variety of impurities including salts, organic acids and remaining biomass all can inhibit the isolation of pure succinic acid or downstream processing of succinic acid containing streams. Because of this, a variety of different solutions have been proposed for the purification of succinic acid, but these solutions have disadvantages.

For instance, a problem with some prescriptions that others have explored is the relatively limited capacity of conventional ion exchange solutions to separate the desired succinic acid. Ion exchange has not been proven a viable processing technique that, can be translated to commercial scale operations. To date, resins have not been shown to have a large enough capacity for succinic acid to provide an efficient sorption process. Hence, adsorption chromatography has been limited by both selectivity and capacity for succinic acid. The use of ion-exchange to remove salts for the fermtentation stream could be applied, but requires the use of acids and bases to regenerate the resins and is only efficient if relatively low levels of salts are present. If the salt content is high in a fermentation broth, an ion exchange system would be retarded and inefficient because of low throughput. Hence, ion exchange resins will be less efficient to separate the salt from other organic acids. Therefore, this is not efficient in cases with high levels of salts. Moreover, traditional ion exchange techniques do not separate easily the different organic acids present in the broth. Electro-deionization (EDI) does not separate the different organic acids to a degree feasible for high-throughput applications because of issues associated with membrane fouling. Other approaches such as reactive extraction require organic solvents and expensive reagents.

Even though all of these techniques have had some success, they have been limited either by cost, byproduct-waste generation, or economy of scale. Hence, for these reasons, a need exists for better or more direct methods for recovery of succinic acid, which can simplify the process and reduce downstream processing costs as well as waste.

SUMMARY Of THE INVENTION

The present invention describes a method of purifying either succinic acid or dibasic succinate from impurities in a fermentation broth. In particular, the process Involves filtering a fermentation broth; adjusting its pH to yield a succinate-containing filtrate having a pH value less than or equal to about 3.0; running the acidified filtrate through a chromatographic column having a non-functionalized resin selectively at an operational temperature in a range from about 20° C. to about 100° C. such that at least two distinct fractions are achieved, at least one of which contains free succinic acid or succinate salt.

In another aspect, the invention describes a method of purifying free succinic acid from a fermentation broth, the method involves: filtering a fermentation broth to yield a clarified broth; providing or acidifying said clarified broth to a pH value of less than 3.0; introducing the clarified filtrate into a continuous chromatographic apparatus having a non-functionalized resin at art operation temperature predetermined for a particular resin employed to separate free succinic acid; and crystallizing the succinic acid.

An advantage of the process is that the free acid can be crystallized to yield a product of 90% or greater purity after a single crystallization. To separate a dibasic succinate salt, the free acid can be eluted later with a strong inorganic base during the chromatographic separation.

In another aspect, the invention describes a method for producing a succinate salt. The method involves: filtering a fermenation broth to yield succinate-containing filtrate, the filtrate having a pH of less than 3.0; processing the filtrate through a liquid chromatographic column over a non-functionalzied resin at a temperature up to about 70° C. eluting with a strong base or organic solvent to form succinic salts.

Further, another advantage is that one can isolate a stream of dibasic species, such as diammomum succinate, which allows for possible direct transformation to a variety of nitrogen containing derivatives including N-methyl succinamide, N-methyl-pyrrolidinone, pyrrolidinone and N-vinylpyrrolidone. As a feature, the present invention opens an easier, simpler, and more cost effective way to achieve a cleaner precursor material for conversion in downstream processing.

In another aspect of the invention, one can adapt the foregoing concept for high-throughput or continuous separations. One can implement a simulated-moving-bed (SMB) chromatographic system for the primary application.

Additional features and advantages of the present purification process will be disclosed in the following detailed description. It is understood that both the foregoing summary and the following detailed description and examples are merely representative of the invention, and are intended to provide an overview for understanding the invention as claimed.

BRIEF DESCRIPTION OF FIGURES

FIGS. 6A, 6B, and 6C depict the plots of a series of pulse tests for isocratic separations, each run at a temperature of 60° C., but with varied pH values for the feed: FIG. 6A is at pH of 2.5; FIG. 6B is at pH of 3.0; and FIG. 6C is at pH 4.3.

DETAILED DESCRIPTION

Section I—Definitions

Before describing the present invention in detail it is understood that the terminology used to describe particular embodiments and is not intended to be limiting. As used in this specification and the appended claims, the singular forms "a," "an," and "the" include plural referents unless the context clearly indicates otherwise. Unless defined otherwise in context, all technical and scientific terms used herein have their usual meaning, conventionally understood by persons skilled in the art to which this invention pertains.

The term "fermentation" as used herein refers to the process of bio-conversion and bio-production of organic acids, alcohols and other chemical materials of interest. The term comprises one or more of the conversion or production processes, occurring alone, sequentially or together, and at any growth state (stationary, plateau, replicating, etc.) of a microorganism.

The term "fermentation broth" refers to a liquid medium in which microorganisms convert organic carbon sources to produce other organic materials of interest.

The term "carbon source" refers to any resource of carbon that is capable of being metabolized by a microorganism where the source contains at least one carbon atom. Sources of carbon may include, for example, various carbohydrates such as dextrose, glucose, fructose, sucrose, starches, etc., alcohols, organic acids and their corresponding salts, or oils, tats, and triglycerides from plants or annuals.

The term "bed volume" or "column volume" refers to the total volume of the packing material and interstitial liquid. The minimum volume of solvent necessary to wet the defined quantity of sorbent within the column cats vary on the nature of the sorbent (e.g., ~120 µl per 100 mg of silica gel sorbent 60 Å, compared to ~600 µl per 500 mg of silica gel sorbent 60 Å).

The term "chromatographic resolution" refers to the degree of separation between consecutive analytes emerging from a chromatographic column.

The term "isocratic elution" refers to a liquid chromatography (LC) separation in which the composition of the mobile phase remains constant throughout the separation process. Isocratic elution is typically effective in the separation of sample components that are not very dissimilar in their affinity for the stationary phase.

The term "gradient elution" refers to a separation in which the composition of the mobile phase is changed or varied during the chromatographic analysis, in particular, the term "binary elution" refers to a separation using two different kinds of elution media.

Section II—Description

The present invention describes, in part, a process of producing chemical feedstock molecules from free organic acids derived from a fermentation broth. As used herein the term "free organic acid" refers to an organic acid compound that is in its protonated state when in solution (i.e., at or less than its pKa value). The present separation process can be employed to recover either the free acid or its salt. According to the present process, separation of free acid is an isocratic elution and salt-generation is a gradient or binary elution. An isocratic elution method is usefulfor a high-volume and cost effective way to separate succinic acid from the other organic acids, sugars, and salts, etc.

The present inventive process employs a hydrophobic, non-functionalized resin bed for chromatographic purification. Of particular interest is the ability of the present process to separate either free succinic acid or succinate salt from other organic acids, salts, and dissolved sugars present in the broth filtrate. Depending on the chromatographic conditions, either a stream of purified succinic acid or dibasic succinate can be isolated. One can selectively operate the separation process to isolate either succinic acid or the dibasic succinate by varying the elution conditions. The operational temperature can be in a range from about 20° C. to about 100° C. In certain embodiments depending on the particular chromatographic resin employed according to the invention, succinic acid is isolated at elevated temperatures, and dibasic succinate is isolated at lower temperatures with a binary elution. The operating temperature for the separation is determined by the equilibrium binding constants, peak shape and resolution of the succinic acid vs. the impurities.

This type of purification is beneficial because it provides a robust method to isolate succinate streams from the residual salts, nitrogen containing impurities and other organic acids all in one step while avoiding some of the inherent Issues with other purification methods, such as fouling of electrodialysis membranes, use of organic solvents, low capacity of ion exchange resins, and sensitivity of crystallization. Given the disadvantages of conventional ion exchange resists that require the use of acids/bases for regeneration and have shown poor capacity for succinic acid in sorption processes, a new, more streamlined approach to the purification process using chromatography would be appreciated.

Unlike with conventional ion exchange chromatography, a non-functionalized resin bed does not exchange salts nor do they need to be regenerated. Hence, the present process saves both time and costs when performing separations either as a discontinuous batch or, optimally, a continuous process chromatography.

Specifically, the process for purifying succinic acid from a fermentation broth involves: filtering a fermentation broth; adjusting pH to yield a succinic acid-containing filtrate having a pH value less than or equal to about 3.0; running the acidified filtrate through a chromatographic system, such as a simulated-moving bed (SMB) system, employing a non-functionalized resins at an operational temperature that is optimized for the particular resin employed. The operational temperature for particular non-functional poly(styrene-divinyl benzene) (PS-DVB) resins is determined through she collection of empirical data in regards to the equilibrium binding constants, retention times and peak resolution. As an example, for a non-functionalized chromatographic resin such as XAD-4, the operating temperature can be either a) greater than 50° C. to produce a tree succinic acid or b) less than 50° C. to produce a salt of succinic acid; such that at least two distinct fractions are achieved. However, other resins may either permit or require that the operational temperature extends higher or lower, for instance, up to about 65° C. or about 70° C. for production of dibasic succinate.

This process provides a possible way to purify a stream of succinic acid from the large majority of other contaminants that are typically found in a fermentation broth in a single operation. An advantage of the present invention is that one can yield high purity (≥90%) succinic acid or its salt in one round of crystallization following chromatography, without prior purification. With optimization, the process can achieve a level of purity that may be as high as, for example, about 92% or 95%, up to about 97% or 99%.

According to a feature of the present separation process, a distinct peak of the succinic acid appears within 3 bed volumes. Typically, the distinct peak is observed between about 1.0 and about 2.75 bed volumes. Salts and other organic acids and byproduct compounds can be easily separated from the desired succinic extraction. This feature can result in the isolation of a "clean" stream (i.e., ≥85% or 90%) of succinic acid/suecinate with very little product loss. One can achieve at least about 68% or 70% (typicaily, about 72% or 75%) recovery of the free acid and salt forms from the filtrated broth. The recovery rate from raw filtrate can be about 80%, 85% or more, and with optimization one can recover either the acid or salt, forms at about 90% to 95% or greater yield from initial feedstock.

A.

In part, the present invention contributes to a refinement of chromatographic separation techniques for difficult to purify organic species. The inventive approach compares favorably to conventional approaches, in that it can be more efficient and cost effective than different processes. A feature of the invention involves a discovery of an operational regime created by a balance of several parameters, including temperature, pH, and elution conditions, before and during the chromatographic process.

According to a feature of the invention, we adapt liquid chromatography (LC) techniques to purify in a single operation a stream of succinic acid from the large majority of other contaminants that are typically found in a fermentation broth. LC typically utilizes different types of stationary phases (i.e. sorbents) contained in columns, a pump that moves the mobile phase and sample components through the column, and a detector capable of providing characteristic retention times for the sample components and area counts reflecting the amount of each analyte passing through the detector. Analyte retention time varies depending on the strength of its interactions with the stationary phase, the composition and flow rate of mobile phase used, and on the column dimensions. Here, relatively large diameter columns and large particle sizes are employed to avoid pressure.

As stated previously, a variety of methods have been explored for the purification of succinic acid including reactive extraction, electrodialysis crystallization and ion exchange, but each has met with problems. To overcome such problems, the present invention employs non-functionalized resins. Non-functionalized resins do not bind the different species by means of an ionic charge, rather, non-functionalized resins work by a balance of hydrophilic and hydrophobic affinities. In the embodiments described, the adsorbent resins are unmodified and considered to be hydrophobic resins. Thus, hydrophobic organic species can bind to them and be retained in aqueous systems.

Since the resin is not functionalized adjustment of the pH of the input material is necessary for the succinic acid to nave an affinity for the resin. Hence, the raw filtrate from the fermentation broth should be acidic, with a pH value of less than about 3. The filtered broth can either have an original acidic pH value or may be treated to acidify to a pH of less than 3. In particular, the filtrate has a pH value in the range of about 1.0 to about 3.0. Typically, the pH is about 1.2 or 2.0 up to about 2.8 or 2.9, desirably the pH is in the range from about 1.3 or 1.5 to about 2.5 or 2.7.

In the embodiments, a type of resin employed in the separation of succinic acid can be classified as adsorbent poly (styrene-divinyl benzene) (PS-DVB) resins. The polystyrene is crosslinked with divinyl benzene. PS-DVB resins are an attractive adsorbent for extraction and separation of various types of compounds due to its stability over the pH range of 1-14. PS-DVB resins are known to have hydrophobic surfaces that highly retain non-polar compounds white poorly retaining polar compounds.

Hydrophobic-type PS-DVB resins are commercially available horn a variety of vendors (e.g., Dow Chemical Company, Rohm & Haas Co., Mitsubishi Chemical Corporation, Puroadsorbents. (In comparison non-polar solvents, such as hydrocarbons, etc. most adsorbents exhibit slightly polar or hydrophilic properties and so will adsorb species with some degree of polarity. This polarity is most pronounced with the acrylic adsorbents and the phenolic adsorbents.) Table 1, summarizes some of the physical and chemical attributes of the AMBERLITE™ brand resins.

TABLE 1

| AMBERLITE™ | Matrix | Surface area ($m^2/g$) | Av. Pore diameter (Å) | Mean diam. (μ) | UC D90/D40 | Applications |
|---|---|---|---|---|---|---|
| XAD™4 | pStyDVB* | 750 | 100 | 640 | 1.6 | Removal of aromatic hydrocarbons such as phenols and pesticides from wastes. High surface area and small pores ideal for the extraction of smaller molecules such as phenol. Hydrophobic |
| XAD™16N | pStyDVB* | 800 | 150 | 700 | 1.6 | Removal of aromatic hydrocarbons such as phenols and pesticides from wastes or polar solvents. High surface area and medium sized pores for the adsorption of large color bodies. Excellent regenerability. Hydrophobic. |
| XAD™1180N | pStyDVB* | 500 | 400 | 530 | 1.6 | Removal of very large organic molecules from aqueous solutions or polar solvents Hydrophobic. |
| XAD™1600N | pStyDVB* | 800 | 150 | 400 | 1.2 | Removal of aromatic hydrocarbons such as phenols and pesticides from wastes or polar solvents Monodisperse. Low swelling between solvent and aqueous solutions. High surface area, excellent separation of different organic species in chromatographic processes. Hydrophobic. | pStyDVB = Polystyrene DVB lite Corporation, Lanxess Corporation, etc.). Depending on the manufacturer and the particular specifications of each type of resin, the resin can have a variety of different pore sizes and surface areas, which can affect the physical and chemical nature of the resins, the quality of the separation and therefore the temperatures required for the different protocols. One can use a resin that has a surface area in the range between about 120 $m^2/g$ or 150 $m^2/g$ up to about 1100 $m^2/g$ or 1200 $m^2/g$. Typically, the surface area of the resin is in between about 150 $m^2/g$ or 200 $m^2/g$ to about 800 $m^2/g$ or 1000 $m^2/g$. In particularly adapted resins for certain organic solutions (e.g., corn syrup, fruit juices, HFCS, polyphenols, or natural extracts), the resin has a surface area of about 250 or 300 $m^2/g$ to about 600 or 750 $m^2/g$. The average pore diameter can range between about 50 Å or 100 Å to about 600 Å or 700 Å: typically between about 100 Å or 150 Å to about 450 Å or 500 Å. The mean diameter of the resin particles may range between about 300 μm or 350 μm to about 750 μm or 800 μm; typically, between about 400 μm or 500 μm to about 650 μm or 700 μm. The resins exhibit porosity in the range of about 0.90 or 0.95 ml/g to about 1.40 or 1.52 ml/g; typically about 0.97 ml/g to about 1.18 or 1.25 ml/g.

As the adsorbent resins exhibit non-polar or hydrophobic tendencies, this means that they readily adsorb organic compounds that are highly soluble in water. For instance, a class of commercial ion-exchange resins from Rohm & Haas is AMBERLITE™ XAD™ polymeric adsorbents, which are very porosis spherical polymers based on highly crosslinked, macrometicular polystyrene polymers. Their high internal surface areas can adsorb and then desorb a wide variety of different species depending on the environment in which they are used. For example, in polar solvents such as water, polymeric adsorbents exhibit non-polar or hydrophobic behavior and can adsorb organic species that are sparingly soluble. This hydrophobicity is most pronounced with the styrenic Others have developed purification strategies to lake advantage of such performance characteristics. For instance, in capture/concentration mode, AMBERLITE™ XAD™ media provide an excellent first purification step in the recovery of phenolic compounds or chlorinated hydrocarbons. In some applications XAD resins perform decoloraization. AMBERLITE™ XAD™ adsorbents can be adapted for used in both, batch and (preferably) continuous operations. Other commercially available polystyrenic adsorbent resins, such as PuroSorb™ PAD adsorbents from Purolite, are made from clean monomers and have high surface areas that are free from any contaminants such as salts, metals and other minerals, making them especially suitable for food and pharmaceutical uses. However, such resins appear not to have been proposed or adapted for industrial separation of organic acids, in particular for succinic acid/succinate uses.

B.

Figure 1:
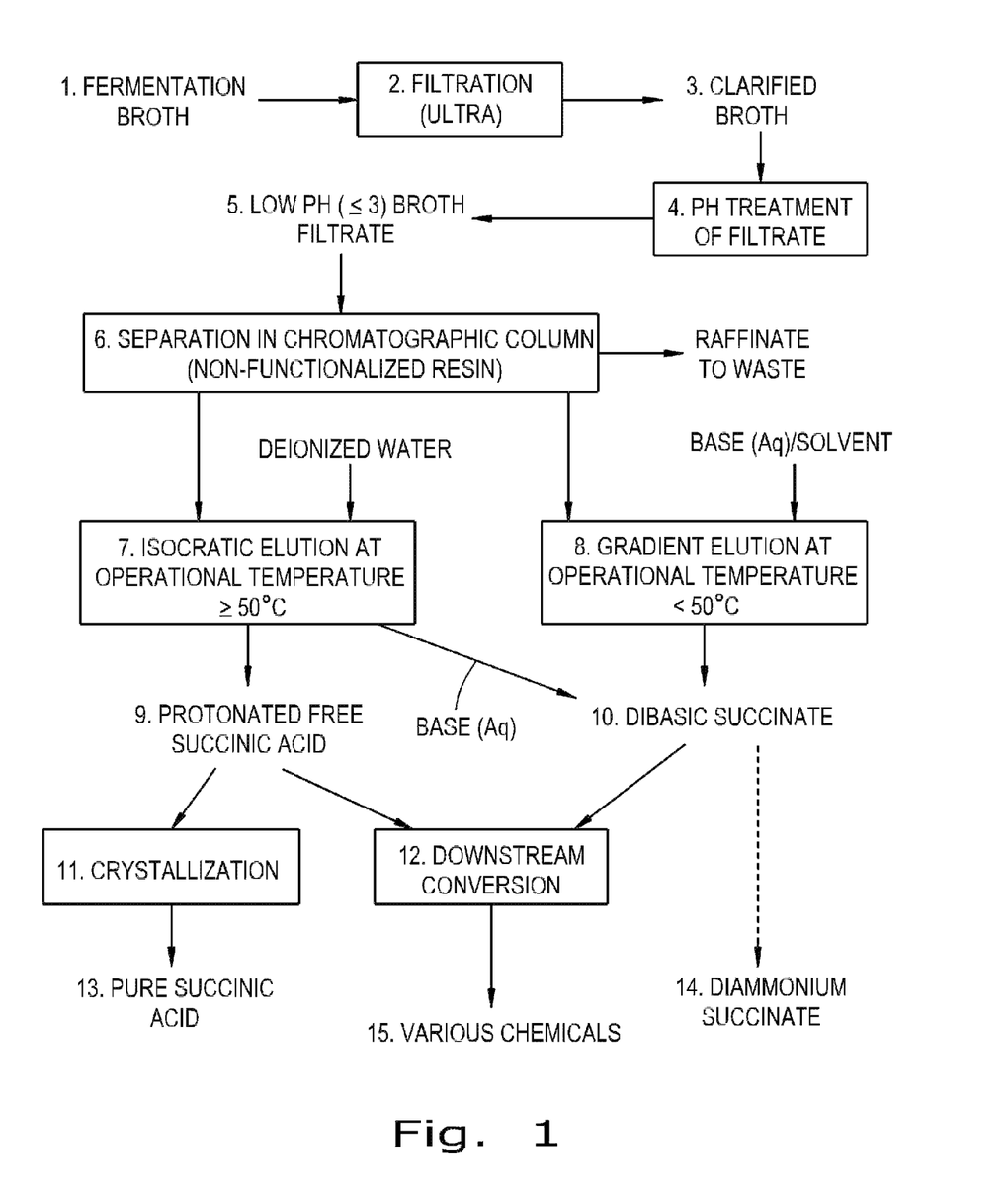
FIG. 1 is a flow chart representing the processing steps according to an embodiment of the present invention.

FIG. 1 is a schematic representation of a separation and purification process, according to an embodiment of the present invention, showing the main products front each of the various processing stages, in general, the separation process involves using a fermentation broth-derived source (1.) of an organic acid, such as succinic acid, filtering (2.) the fermentation broth (1.) to remove biomass and yield a raw filtrate medium (3. ). The raw filtrate (3.) either may have an innately acidic pH value or is treated to acidify (4., 5.) the medium before the filtrate is fed into a chromatographic column (6.) having a non-functionalized resin. The separation can be run selectively according to two different protocols depending on the desired product: protonated acid or dibasic salt, in the free acid-producing separation (7.), the feed is typically processed isocratically with a deionized water elation at an elevated temperature (e.g., an operational temperature of about 50° C. or greater, typically between about 52° C. to about 87° C. for XAD-4). Optionally, if desired, the raw free acid (9.) can then be crystallized (11.) to yield purified succinic acid (13.). In the salt-producing separation (8.), the feed is processed in a binary elution of deionized water and strong base at lower temperatures (e.g., an operational temperature of less than about 50° C., between about 20° C. and about 45° C. for XAD-4) or with an organic solvent, such as methanol, ethanol or acetone. Other PY-DVB resins may have different affinities; hence, they may be processed at different temperatures according to the general parameters. Any strong inorganic, ammonia, or carbonate bases can be used in the process, (e.g., NaOH, KOH, LiOH, $NH_2$, $Na_2CO_3$). Alternatively, as reflected in FIG. 1, one can run an isocratlc elution at elevated temperatures, isolate the succinic acid, and then treat with aqueous base to generate dibasic succinate (10.) (e.g., diammonium succinate (14.)). The products from either route can be subsequently processed chemically (12. ) to yield other commercially important chemicals (15.) (e.g., tetrahydrofuran, 2-pyrrolidone, N-Methyl-2-pyrrolidone (NMP), 1,4-butanediol, 1,4-diaminobutane, succinonitrile, succindiamide, or dibasic succinic ester). As described herein in general terms, various different permutations and iterations are envisioned according to the present invention; hence any of the foregoing procedural steps may be combined with any other step in a method sequence.

In isocratic elution, peak width increases with retention time. Ordinarily, this feature leads to a disadvantage that late-eluting peaks get very flat and broad; hence, their shape and width may keep them from being recognized as peaks, in the present isocratlc elution system, one of the advantages is that the sample retention time has been shortened from conventional operative parameters. The peaks of the later-eluting species have been concentrated and amplified. This feature has greatly increased the potential for high-throughput processing in short duration and in an economic and efficient manner. In particular, when using a resin like XAD-4 at lower temperatures (<40° C.), the succinic acid elutes at long elution times and with a broad peak shape. By increasing the temperature the peak shape and retention time both improve. Additionally, by performing a binary elution with a basic solution or organic solvent the slow eluting succinic acid peak is eluted much more quickly and at higher concentrations. Both of these treatments result in a greatly increased potential for high throughput processing in an economic and efficient manner.

As the accompanying pulse tests with XAD-4 illustrate, separations of succinic acid can require running the separation for more than three (3) bed volumes before a peak of elution appears and the peak would tend to be very broad at ambient temperatures, making the elution more difficult to discern. In contrast, according to the present disclosure, one can achieve a good, distinct separation of succinic acid from the other organic acids, dissolved salts and sugars, etc. in the broth filtrate within three (3) bed volumes by adjusting the operating temperatures. Typically, a distinct peak appears within about 2.8 bed volumes. As shown in the accompanying FIGS. 2-9, one can observe a distinct peak of succinic acid between about 0.8 or 1.0 and about 2.5 or 2.75 bed volumes. The chromatographic resolution (i.e., degree of separations between the succinate peak and those of salts and other organic acids can be between about 0.1 or 0.2 bed volumes to about 0.5, 0.75, or 1.0 bed volumes. Depending on the input concentrations, the amount of the succinic acid produced per liter can be significantly more than that of the other organic acids.

While the operating temperature for different non-functional resins may change based on the equilibrium binding constants, retention times and peak resolution, for XAD-4 the operational temperature for free-acid separation is typically between about 50° C. and about 90° C., while the operational temperature for salt generation is between about 20° C. and about 50° C. When the purification process is run at a temperature of about 50%; or greater, we observed that the resolution, peak shape and retention time improved for the free acid, and possibly also the separation rate and efficiency. With an increase in temperature, the retention time of succinic acid under isocratic conditions can be improved to under about 2.0 bed volume resulting in an efficient SMB system, such as shown in FIGS. 2, 3, 4, and 5. A higher operational temperature is in a range between about 50° C. or 53° C. to about 88° C. or 90° C., inclusive. More particularly, the temperature is between about 55° C. or 58° C. to about 83° C. or 85° C., and desirably between about 60° C. or 65° C. to about 78° C. or 80° C. Operational temperature ranges between about 55° C. or 60° C. and about 70° C., 75° C. or 85° C. may be good for industrial processing. The operating temperature of the non-functional resins can be up to about 150° C., with specific resins at temperatures between about 65-90° C. typically about 72° C. to about 80° C.

In addition to separating the succinate from salts, the present process allows one to precipitate and recover metal salts from the raffinate if desired without losing succinate to the filter cake or exposing the succinate to the recovery conditions. When the isocratic elution is executed at ambient room temperature (i.e., ~20° C.-25° C.) with XAD-4, the elution tended to be relatively slow and not practical or adaptable for high-volume commercial processing, such as SMB chromatography. The appearance of a separate succinic peak often would lake a residence or retention time that exceeds 2.75 or 3 bed volumes. Binary elution decreases the retention of the later-eluting components so that they elute faster, giving narrower (and taller) peaks for most, components. This also improves the peak shape for tailed peaks, as the increasing concentration of the eluate pushes the falling part of a peak forward. This also increases the peak height (the peak looks "sharper"), which is important for efficiency. For XAD-4 the operational temperature for salt separation is between about 22° C. or 24° C. to about 44° C. or 48° C.

Gradient or binary elution decreases the retention of the later-eluting components resulting in an improved peak shape for succinic acid. The later-eluting components appear to elute taster, giving narrower (and taller) peaks for most components. In turn this results in a higher concentration of the product and a more efficient chromatographic process. This also increases the concentration of succinic acid as the eluent pushes the tailing part of a peak forward, which increases the peak height (i.e., the peak looks "sharper"), which is important In trace analysis. The gradient program may include sudden "step" increases in the percentage of the organic component, or different slopes at different times—all according to the desire for optimum separation in minimum time. The operational temperature for salt separation is between about 22° C. or 24° C. to about 44° C. or 48° C.

Figure 3:
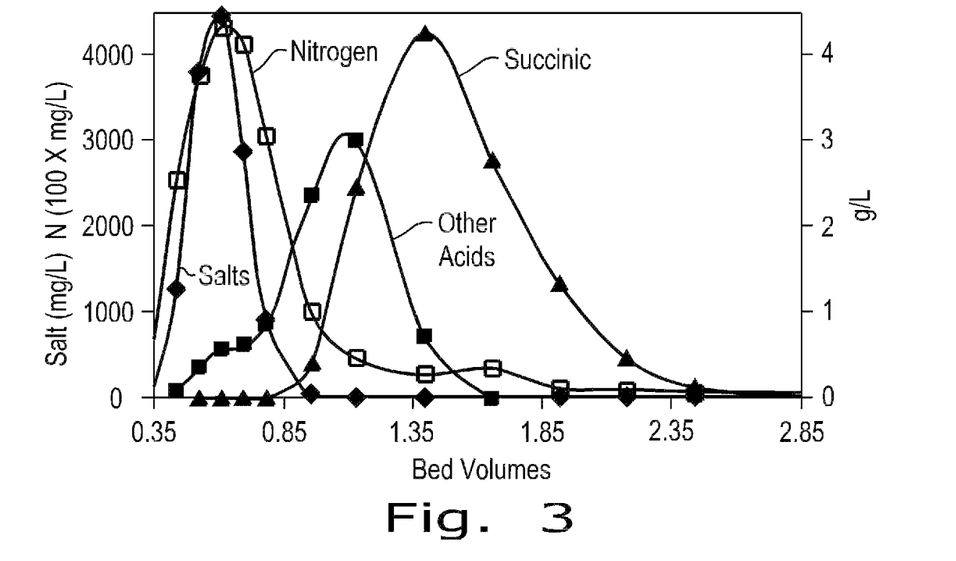
FIG. 3 shows the plot of a pulse test for an isocratlc separation like in FIG. 2, run at a temperature of about 60° C.
Figure 4:
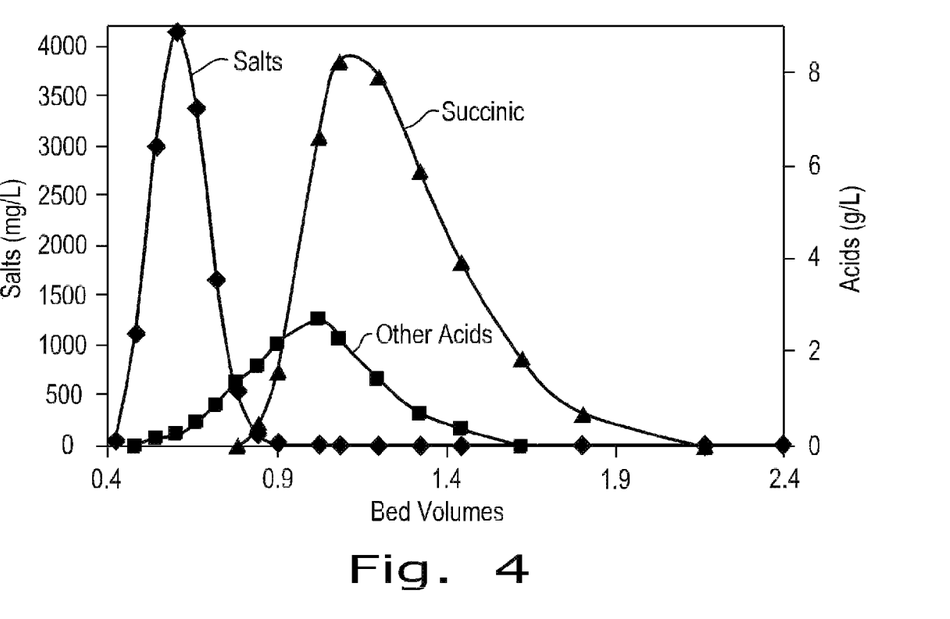
FIG. 4 shows the plot of a pulse test for an isocratic separation like in FIG. 2, run at a temperature of about 75° C.
Figure 5:
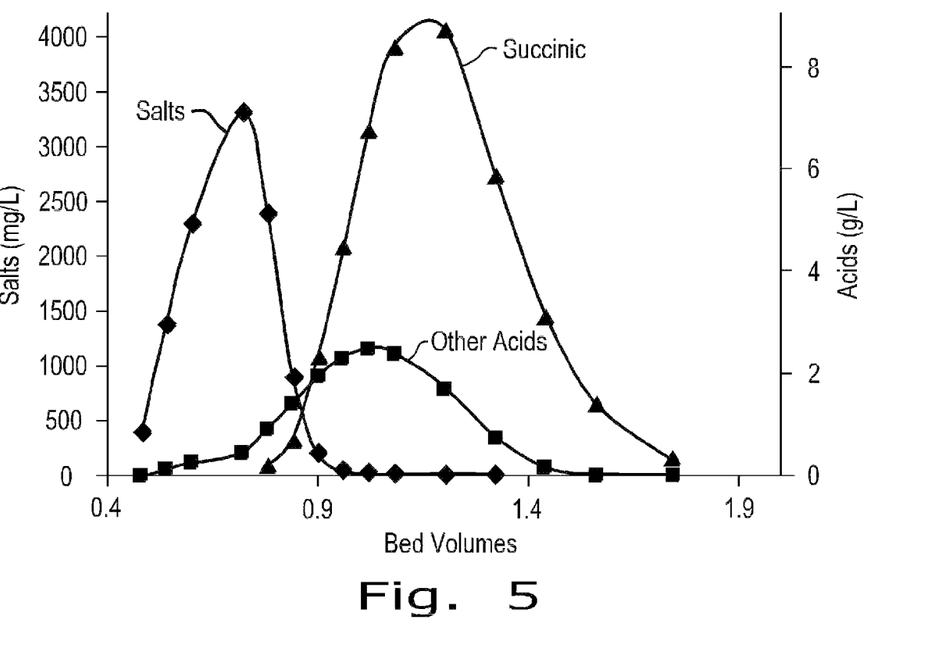
FIG. 5 shows the plot of a pulse test for an isocratic separation like in FIG. 2, run at a temperature of about 90° C.

FIG. 3, also shows that the present separation process can readily remove both salts and nitrogen containing compounds, such as amino acids or urea, which may remain, in solution after filtering. The nitrogen compounds are removed early within the first bed volume. The distinct resolution between the different species can be amplified in simulated continuous moving-bed systems for even better separation.

Figure 6A:
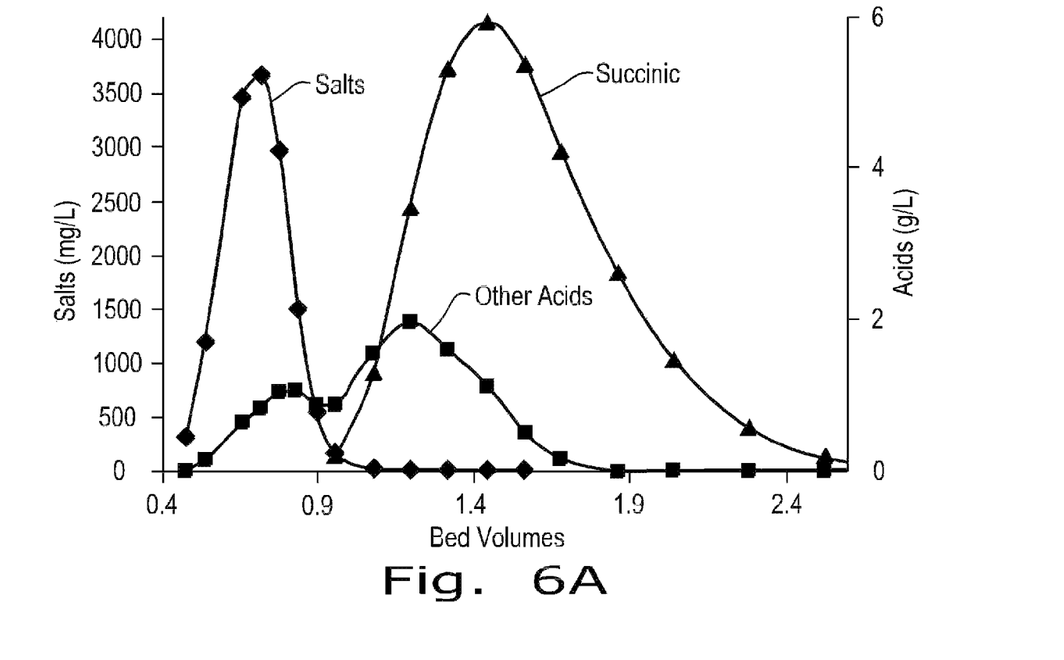
Figure 6B:
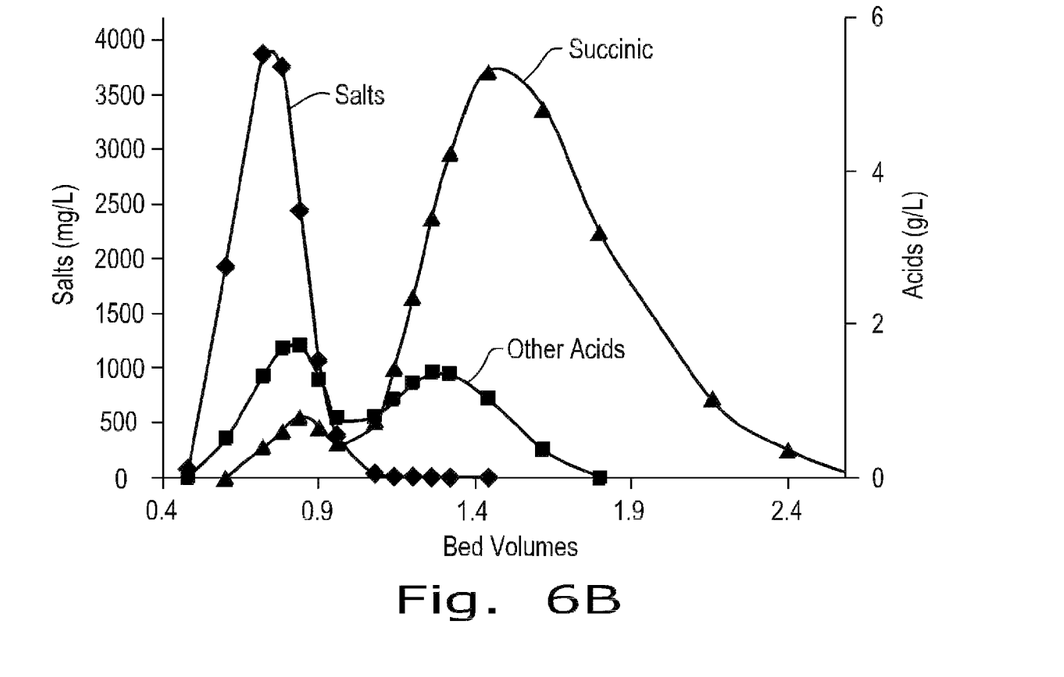
Figure 6C:
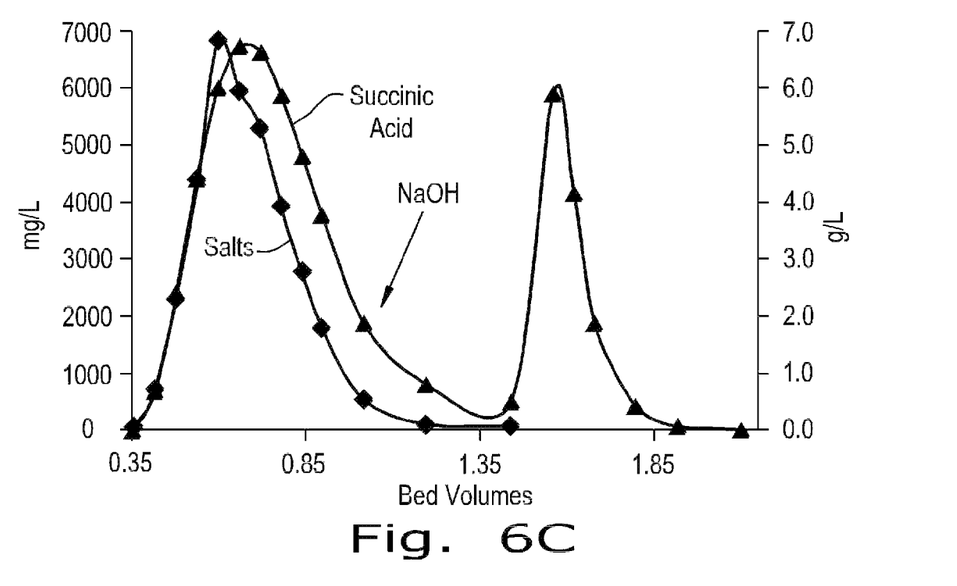

As illustrated in the accompanying FIGS. 6A-6C, the feedstock medium should be processed at a low pH value of less than or equal to about 3.0. Typically, for good chromatographic performance the pH value is not greater than about 2.8 or 2.5. FIG. 6A depicts a plot of a pulse test in which the separation was run with a feed pH of 2.5. The pulse test shows good resolution between succinic acid., salts, and other organic acids, and distinct peaks for each species. Similarly. FIG. 6B is a plot of a pulse test, for a feed pH of 3.0. The resolution of the succinic acid, salts and other organic acids is still good, but a small amount of succinic acid may be lost potentially to the raffinate as one notices a small rise in the succinic separation curve between about 0.5 and 0.9 bed volumes. The pulse test of FIG. 6C is run with a feed pH of about 4.3. As is apparent in FIG. 6C when the feedstock has a higher pH than about 3.0, the other salts and impurities tend to overlap closely with the succinic acid extraction: hence, separation of succinic acid from the salts tends not to resolve distinctly.

Figure 7:
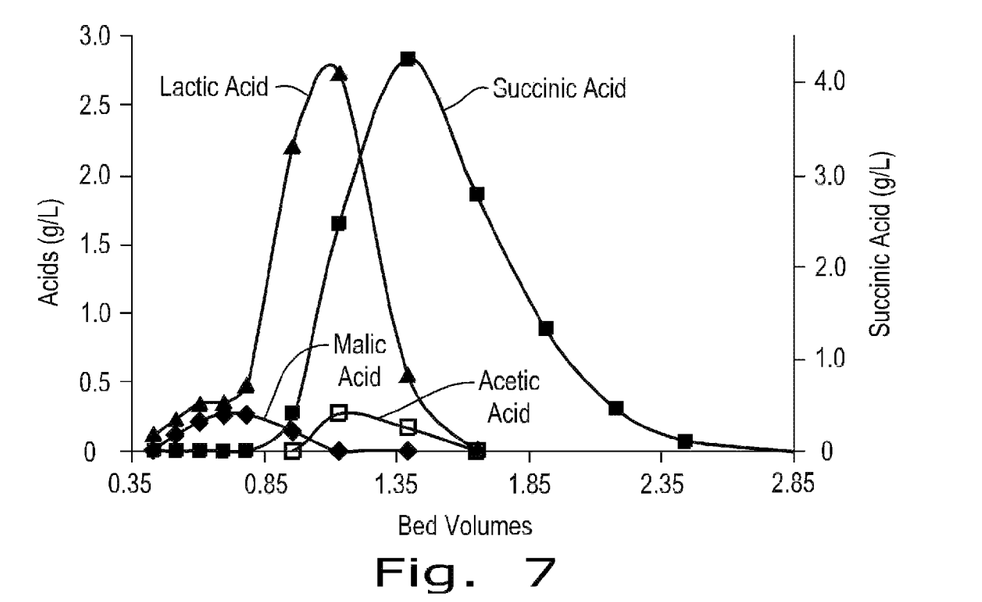
FIG. 7 shows the plot of a pulse test of an isocratic separation like in FIG. 3, run at a temperature of about 60° C. The plot shows the distinct peak for succinic acid and its separation from other organic acids.

FIG. 7 snows the relative effectiveness of the present process to separate various different kinds of organic acids. The resolution for malic, lactic, and acetic acids from succinic acid can be achieved in a continuous chromatographic system (e.g., simulated-moving bed (SMB)).

Accordingly, we envision an embodiment in which the present process makes feasible and commercially efficient the separation of succinate from fermentation broths on non-functionalized resins using SMB chromatography. SMB typically utilizes different types of stationary phases (i.e. sorbents) contained in columns, pumps that move the different mobile phases and some sort of device to 'move' the stationary phase counter currently in regards to the liquid flows. Pulse tests discussed In the following section provide a basis to evaluate different conditions and resins for application in SMB chromatography. SMB chromatography can be optimized to purity a stream of succinic acid in a continuous fashion.

Section III—Empirical Examples

According to embodiments of the present invention, a source of succinate is derived from fermentation. As an initial step, the separation and purification process involves ultra-filtering the fermentation broth to remove cell mass, cellular-debris, proteins and other insoluble materials to yield a succinate-containing raw filtrate. The filtrate can either have an innate pH value less than or equal to about 3, or the filtrate can be acidified to a pH of less than 3.0. Then, processing or running the raw nitrate through a chromatographic column.

All pulse tests In the experimental examples were performed on non-functionalized chromatographic resins. The specific temperature range of operation for the separation may change or may be adjusted if one were using other non-functional resins from other manufacturers. We use pulse tests to demonstrate the functional feasibility of SMB systems. Persons of skill in the art understand that the separation performance of other particular non-functional resins may be either better or worse than that which is shown in the results and ranges of the presersi examples, and should be adjusted and optimized as each individual case may dictate.
Chromatographic Parameters:

Using a non-functional hydrophobic resin (AMBER-LITE™ XAD-4 from Rohm & Haas Co.), a number of pulse tests are performed. The tests demonstrate good separation between succinic acid and a variety of impurities, in the examples, ail pulse tests were performed in 1.5 cm jacketed glass columns with 100 ml of resin. The chromatographic resins in columns are packed as a slurry using down-flow. The resin was thoroughly washed with deionixed water prior to testing. A 6 ml pulse of the feed was charged, and elated with deionized (DI) water at a flow rate of 3 ml/min. No backpressure was observed.

A. Operational Temperature Range

For XAD-4, we have found that higher temperatures promote better separation results within a reasonable elution volume under isoeratie conditions. If the separation is run at elevated temperatures, one can isolate succinic acid from salts, nitrogen compounds, other organic acids (e.g., alic, lactic, or acetic acids). As the pulse tests in the accompanying Figures demonstrate, the free succinic acid is distinctly separate from all other salts that elute easily with water rinse. Based on the chromatographic separations observed in the pulse tests, protonated succinic acid binds snore strongly to the hydrophobic resin then the impurities including the other organic acids. Generally, the lower the equilibrium constant or dynamic binding, the faster the bound species will tend to elute from the resin. Likely, the converse is also true, in that the higher the equilibrium constant, the slower the species will tend to elute and be retained more. While the tests on XAD-4 indicate that elevated temperatures are required for efficient elution of succinic acid, exact operational temperatures may change depending on the operational parameters of the specific non-functionalized resin used and/or the species of interest.

Examples 1, 2, 3, and 4, illustrate the effect of temperature on the efficiency for separating succinic acid from fermentation broth feedstock using XAD-4 non-functionalized chromatographic resin. To a jacketed glass column (1.5 cm diameter) was loaded 100 ml of XAD-4. The resin is heated to the temperature indicated using a water bath. The resin was washed with ~500 ml of water. A 6 ml pulse of the feed was charged, and dated with de ionized (DI) water at a flow rate of 3 ml/mm. No backpressure was observed.

As the pulse test results indicates when applied to a SMB system, separations performed at operational temperatures lower than 50° C. appear to separate less efficiently, would require use of more elution, and hence more dilution of the desired product. Hence, as data in the examples support, the ability to efficiently separate free succinic acid from the other salts and organic acids in the filtrate is performed in temperature range from about 50° C. to about 90° C. with XAD-4. Typically, the operating temperature is between about 53° C. or 55° C. to about 75° C. or 80° C., and desirably between about 57° C. or 65° C. to about 70° C. or 72° C.

EXAMPLE 1

Purification of Succinic Acid from Fermentation Broth at pH 2 and 50° C.

Figure 2:
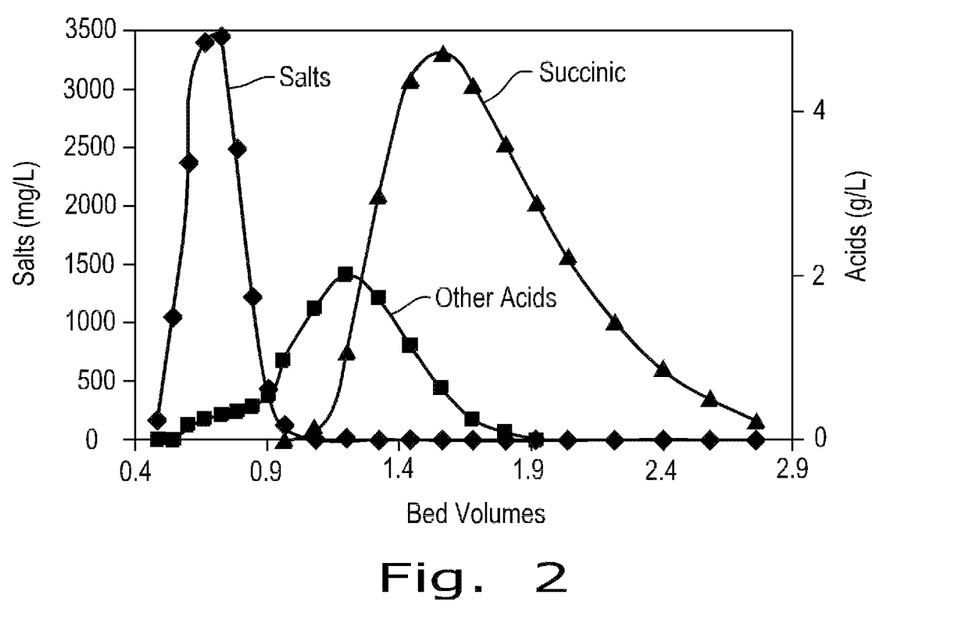
FIG. 2 is graphical illustration of a pulse test derived from an isocratlc separation according to an iteration of the present invention, in which filtrate from fermentation broth at pH 2 is run through a column at a temperature of about 50° C.

FIG. 2 shows the results of a pulse test performed at 50° C. according to a permutation of the present invention. A distinct chromatographic resolution between the succinic acid and other organic acids and salts is shown. The salt peak resolves at about 0.4 bed volumes with a peak at about 0.7 bed volumes. The other organic acids show a peak at about 1.2 bed volumes. The succinic acid starts to resolve at about 0.9 or 1.0 bed volume and reaches a peak at about 1.5 or 1.6 bed volumes. Nearly all of the succinic acid has elated by about 2.8 bed volumes.

EXAMPLE 2

Purification of Succinic Acid from Fermentation Broth at pH 2 and 60° C.

Similar to Example 1, the separation in Example 2, according to the present invention, was performed with the temperature of the jacket in the column heated to 60° C. with a water bath. FIG. 3 summarizes the results of a pulse test performed at 60° C. This resulted in the complete elution of the succinic acid. Also, the figure shows that the succinic acid was effectively separated from the nitrogen containing materials and other organic acids that are common contaminants in fermentation broths.

As would be expected the electro-conductivity in the system tracts closely desorption of other salts. A further detail in FIG. 7 shows a clear distinct resolution of succinic acid against malic, lactic and acetic acids in the raw filtrate. The curve of the succinic acid reaches a pack at about 1.5 bed volumes, while the peaks of the curves of other acid species closely overlap with one another from about 0.75 to about 1.25 bed volumes.

EXAMPLE 3

Purification of Succinic Acid from Fermentation Broth at pH 2 and 75° C.

As with the previous examples performed at 50° C. and 60° C., the elution at 75° C. shows a near complete chromatographic separation of the salts and succinic acid. Also, the elution of other organic acids was relatively good.

EXAMPLE 4

Purification of Succinic Acid from Fermentation Broth at pH 2 and 90° C.

When a chromatographic separation is performed at a temperature at about 90° C., the peaks of the different species start to converge. This feature could result in an increased loss of succinic acid to the raffinate portion, which begins to defeat a purpose of the present invention to maximize succinate amounts in the eluate. This result suggests that operational temperatures above 90° C. may not be beneficial and that, at least for the particular kind of non-functionalized resin used, there may be an upper operative temperature limit.

EXAMPLE 5

Purification of diammoninon succinate from a fermentation broth at pH 2 at 25° C.

A similar pulse test was performed at ambient temperature, however, the NH$_4$OH was not added until about 2.4 bed volumes. In this test it was observed that succinic acid begins to elute at about 1.5 bed volumes and the NH$_8$OH accelerates the elution.

B. Range of pH Values

Similar to examples in the previous section, FIGS. 6A-6C illustrate the effect of pH on the chromatographic separation. FIG. 6A uses a feed that is at pH of 2.5; FIG. 6B is at pH of 3.0; and FIG. 6C is at pH 4.3. The pH value for the feedstock should be less than 3. As one can see from the accompanying figures the pulse test results at pH 2.5 shows good separation and elution, but once the pH value is raised to 3 or above the succinic acid peak becomes bimodal. This would result in loss of product to the raffinate. To minimize occurrences of bimodal peaks for the desired succinic acid in separation, it appears that a good operational range for pH value begins between about 2.5 and 3, and may tend lower to about 1.3 or 1.0, or further.

C. Binary Elution

EXAMPLE 6

Purification of Disodium Succinate from a Fermentation Broth at pH 2.0 and 40° C.

Figure 8:
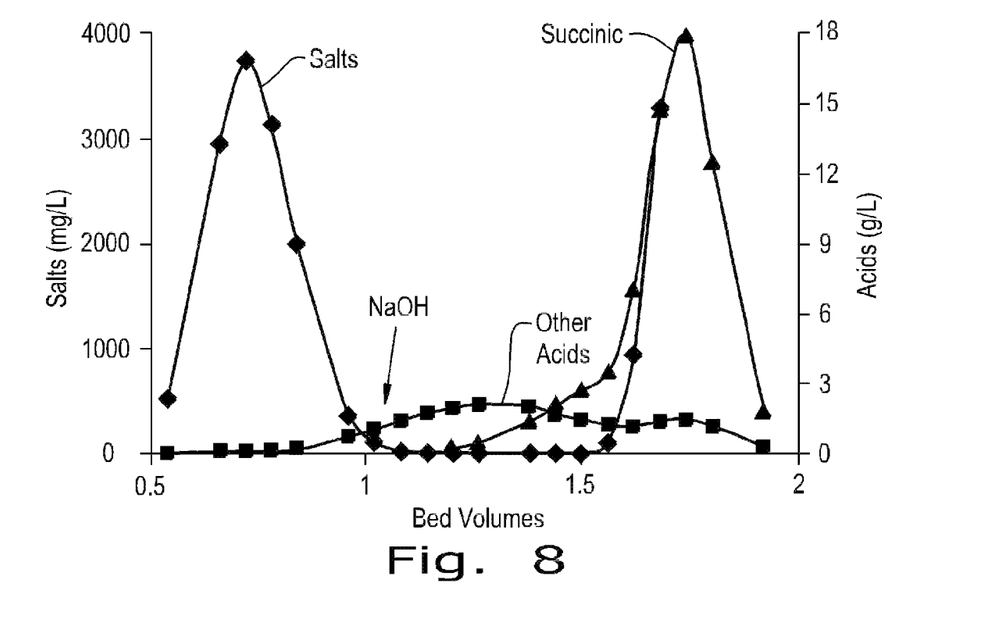
FIG. 8 shows the plot of a pulse tests derived from a gradient or binary elation with a base (e.g., NaOH) at an operative temperature of about 40° C. and a feed pH of 2, according to another embodiment of the present invention.

FIG. 8 shows an initial pulse test, in which 6 ml of the fermentation broth containing ~50 g/L succinic acid was loaded onto the column at ambient temperature followed by elution at 3 ml/mm with deionixed water. After observing the conductivity drop (salts had eluted) the eluent was switched to 5% NaOH. The resulting analysis revealed that, the salts were completely separated from the disodium succinate.

EXAMPLE 7

Purification of Disodium Succinate from a Fermentation Broth at pH 2.0 and 25° C.

Figure 9:
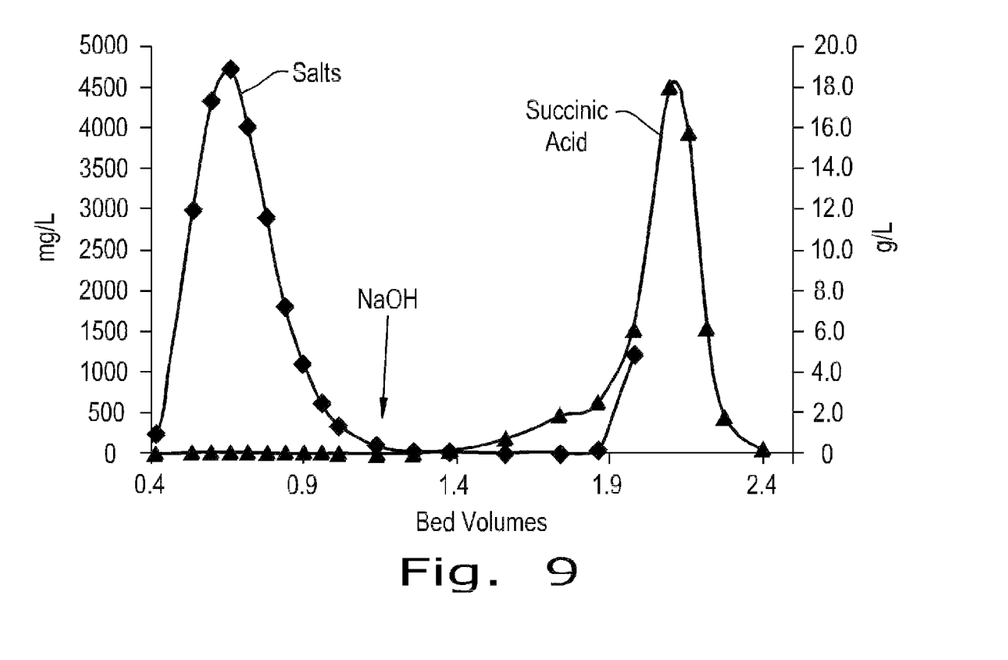
FIG. 9 shows the plot of a pulse test for a binary elation like in FIG. 8 run at a temperature of 25° C. and a feed pH of 2.

FIG. 9 shows a pulse test similar to that in Example 6, however a temperature of 25° C. was used. Once again, there was a complete separation between the succinate and the salts.

EXAMPLE 8

Purification of Diammonium Succinate from a Fermentation Broth at pH 2.0

Figure 10A:
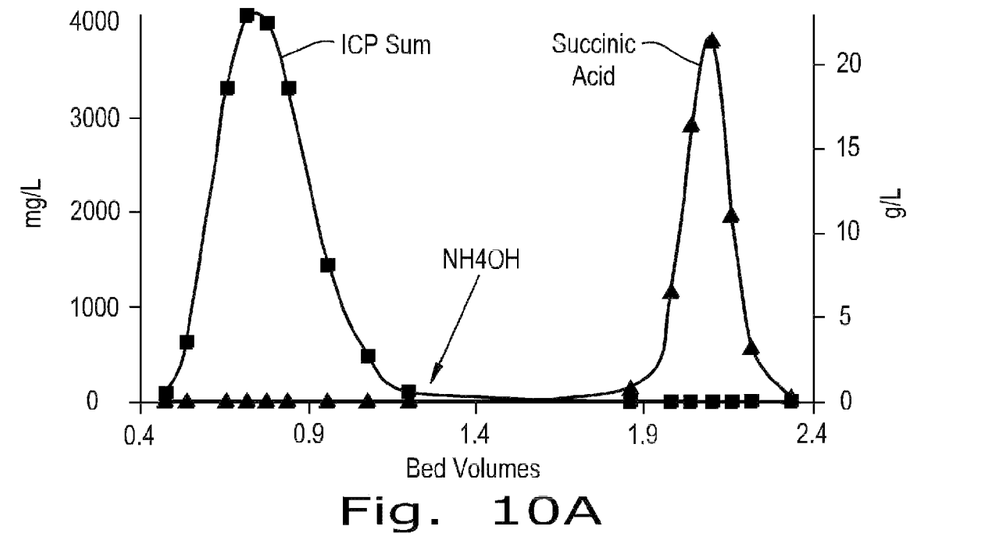
FIG. 10A shows the plot of a pulse test for a binary elution with $NH_4OH$, run at a temperature of 25° C. and a feed pH of 2.
Figure 10B:
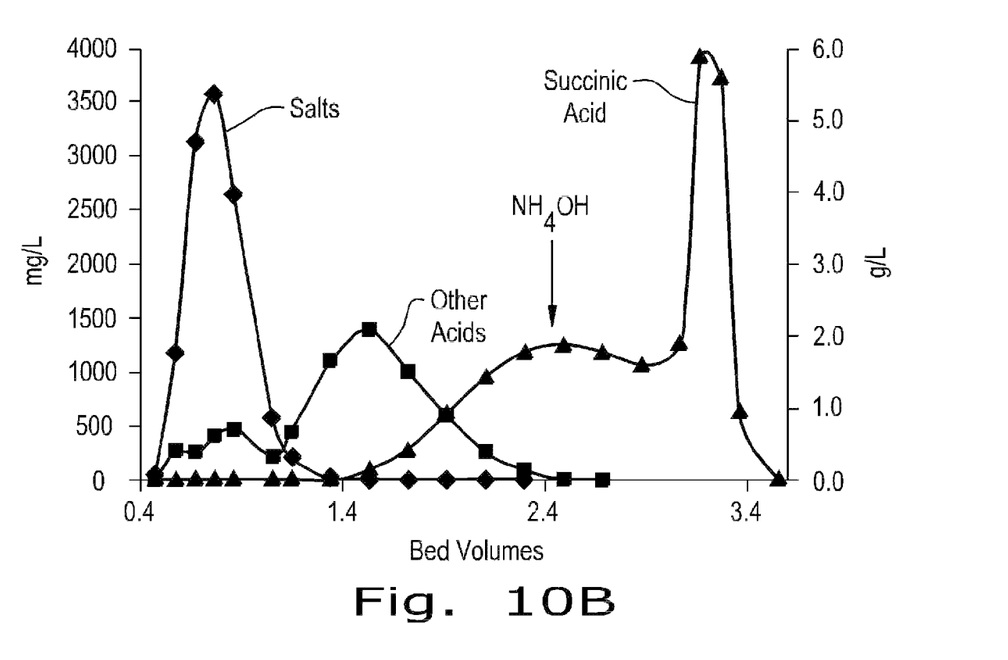
FIG. 10B shows the plot of a pulse test for a gradient elution like in FIG. 10A, but with a late addition of base to demonstrate that succinate does elute as a salt at ambient temperatures with a sharp peak.
Figure 11:
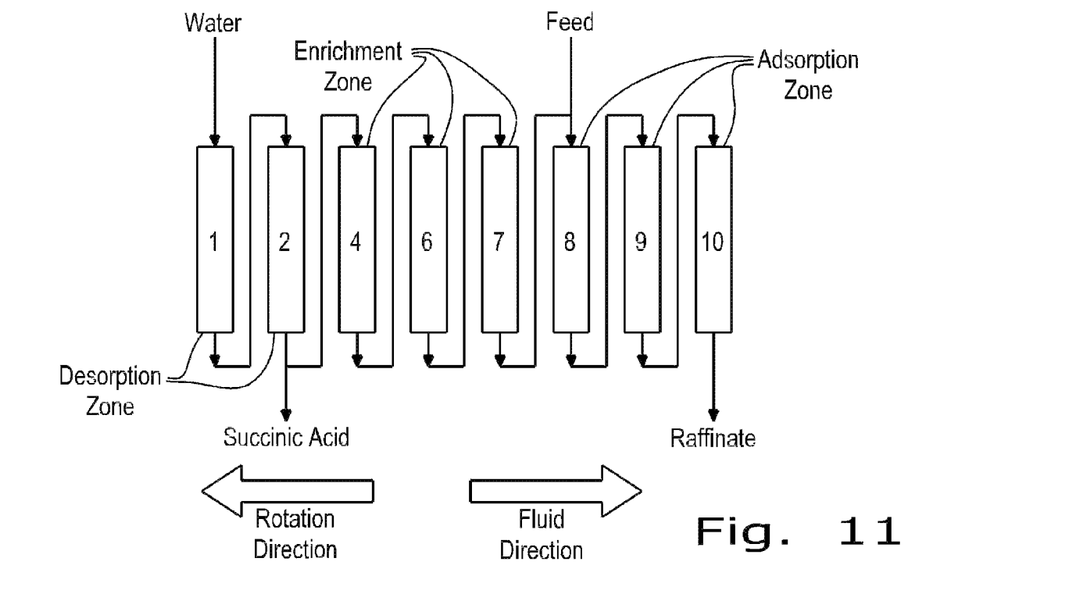
FIG. 11 shows a schematic representation of a simulated moving bed chromatographic system adapted to elute succinic acid (protonated) according to an iteration of the present invention.

FIG. 10A shows another pulse test performed similarly to that of Example 6; however, NH$_4$OH was used as the second eluent. This resulted in a stream of diammonium succinate which can be potentially used in downstream processing to form other nitrogen containing products, such as the commercially desirable N-methyl pyrrolidinone.

D. Elution Conditions

Binary Elution for base elution of dibasic succinate with XAD-4, the operating temperature range is about 20° C. to about 40° C. Non-functional resins could be used to separate succinate directly at ambient temperature away from the salts and other acids. In one example, to a jacketed glass column (1.5 cm diameter) is loaded 100 ml of XAD-4 resin. The resin is heated to the appropriate temperature (about 22-25° C.) using a water bath. The resin was washed with ~500 ml of DI water. A 6 ml pulse of the fermentation-derived feed is charged, and elated with DI water at a flow rate of 3 ml/mm. At an appropriate time (e.g., within about 1.2-2.0 or about 2.5-3.0 bed volumes, inclusive), a 5-10 wt. % solution of base was used as the eluent to create the succinate salt. (Although, both NaOH and NH$_4$OH were employed, any strong, inorganic base such as NH$_2$, LiOH or KOH, can work.) No backpressure is observed. Additional experiment for base elution of dibasic succinate is performed at 40° C., using NaOH or KOH to elate. From the empirical data summarized in FIGS. 8-10, it appears that once the temperature is raised above 40° C., the ability to purify succinic acid from the other organic acids will be difficult on XAD-4; hence, isocratlc purification would be a better approach.

Isocratic Elution:

Like above 100 ml of XAD-4 resin is loaded into a jacketed glass column (1.5 cm diameter). The resin is heated to about 60° C. using a water bath. The resin Is rinsed with about 500 ml of DI water. A 6 ml pulse of the fermentation-derived feed is charged, and eluted with DI water at a flow rate of 3 ml/min.

The temperature is maintained constant, throughout the elution. No backpressure is observed.

Incomplete elution of the compound of interest will occur if the sorbent mass is too large for the volume of solvent, used. Incomplete retention of compound of interest will occur if the sorbent mass is inadequate, leading to compound eluting in the fraction or in the wash solvent. Such cases may lead to lower recovery rates.

Figure 12:
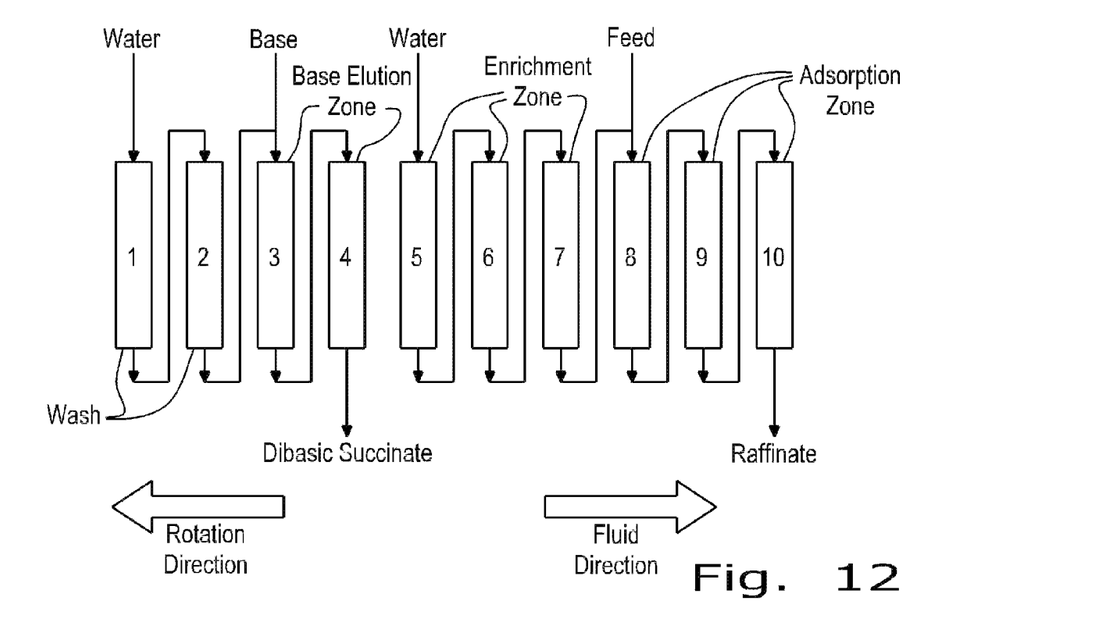
FIG. 12 is a schematic representation of a simulated moving bed chromatographic system adapted to elute deprotonated succinic salt (e.g., diammonium succinate).

For persons skilled in chromatography, the results summarized in the accompanying figures suggest that the present process is adaptable for continuous separation of succinic acid using simulated-moving bed chromatography. We envision using isocratic conditions and adapting the temperature of the operation to best fit the performance of particular resins, which likely is at an elevated temperature. Also, one can apply the results to continuous separation of dibasic succinate using simulated moving bed chromatography. In this instance it would be in a 4 to 5-zone system using both water and a basic solution. This process can provide a simpler and cleaner way of reacting succinate with NH$_4$OH to produce diammonium succinate, which can be used as precursor material for other chemicals, in addition it is envisioned that succinic acid could be isolated as a stream in solvent water by using an organic solvent, such as alcohol as the eluent in a similar arrangement as that in FIG. 12. This would result in a stream of succinic acid that could be used in directly in downstream processing.

The present invention has been described in general and in detail by way of examples. Persons of skill in the art understand that the Invention is not limited necessarily to the embodiments specifically disclosed, but that, modifications and variations may be made without departing from the scone of the invention as defined by the following claims or their equivalents, including other equivalent components presently known, or to be developed, which may be used within the scope of the present invention. Therefore, unless changes otherwise depart from the scope of the invention, the changes should be construed as being included herein.

We claim:

1. A process for obtaining a succinate product from a fermentation broth comprising:
   filtering the fermentation broth to obtain a succinate-containing filtrate;
   ensuring that the succinate-containing filtrate has a pH of about 3.0 or less;
   running said succinate-containing filtrate through a chromatographic column having a non-functionalized resin at an operational temperature in a range of about 20° C. to about 100° C.,
   wherein said operational temperature is selected to produce a column eluent that is selectively either enriched in free succinic acid relative to a salt of succinic acid, or enriched in a salt of succinic acid relative to free succinic acid.

2. The process according to claim 1, wherein said operational temperature is either a) greater than 50° C. to produce said eluent enriched in free succinic acid, or b) less than 50° C. to produce said eluent enriched in said salt of succinic acid.

3. The process according to claim 2, wherein said operational temperature for producing said eluent enriched in free succinic acid is between about 50° C. to about 90° C.

4. The process according to claim 2, wherein said operational temperature for producing said eluent enriched in said salt of succinic acid is between about 20° C., to about 45° C.

5. The process according to claim 1, further comprising crystallizing succinic acid from said eluent enriched in free succinic acid.

6. The process according to claim 5, wherein said crystallized succinic acid exhibits >90% purity after a single crystallization.

7. The process according to claim 1, wherein said eluent enriched in free succinic acid manifests as a distinct chromatographic peak within 3 bed volumes of elution of said column.

8. The process according to claim 1, wherein said succinate-containing filtrate has a pH of about 1.0 to about 3.0.

9. The process according to claim 1, wherein producing said eluent enriched in free succinic acid involves an isocratic elution of said column with deionized water.

10. The process according to claim 1, wherein producing said eluent enriched in said salt of succinic acid involves a binary elution of said column with either a) deionized water and aqueous strong base, or b) deionized water and an organic solvent.

11. The process according to claim 1, wherein said non-functionalized resin is a hydrophobic polystyrene-di-vinyl-benzene (PS-DVB).

12. The process according to claim 1, wherein said chromatographic column is configured in a simulated-moving bed (SMB) chromatographic system.

13. A method for producing a succinate salt comprising: filtering a fermentation broth to yield a succinate-containing filtrate; ensuring that said filtrate has a pH of 3.0 or less; processing said filtrate through a liquid chromatographic column over a non-functionalized resin at a temperature of up to 70° C., and eluting said chromatographic column with a strong base or organic solvent to obtain an eluent enriched with a succinic salt.

14. The process according to claim 13, wherein said temperature is between about 20° C. and about 45° C.

15. A method of purifying succinic acid from a fermentation broth comprising: filtering a fermentation broth to yield a clarified broth filtrate; ensuring said clarified broth filtrate has a pH of about 3.0 or less; introducing said clarified broth filtrate into a continuous simulated moving bed chromatographic apparatus configured with column comprising a non-functionalized resin, at an operational temperature selected to produce a column eluent that is selectively enriched in free succinic acid relative to a salt of succinic acid; and crystallizing said free succinic acid from said column eluent.

16. The method according to claim 15, wherein said crystalized free succinic acid has at least 90% purity after a single crystallization.

17. The method according to claim 15, wherein said column eluent of free succinic acid manifests as a distinct chromatographic peak within 3 bed volumes of elution of said column.

18. The method according to claim 17, wherein said column eluent of free succinic acid manifests as a distinct peak between about 1.0 and 2.75 bed volumes of elution of said column.

19. The method according to claim 15, wherein said column is eluted by an isocratic elution.

20. The method according to claim 15, wherein said operational temperature is between about 50° C. and 100° C.

* * * * *